United States Patent [19]

Lawes et al.

[11] Patent Number: 5,197,990
[45] Date of Patent: Mar. 30, 1993

[54] PROSTHETIC INTRAMEDULLARY FEMORAL PROSTHESIS WITH PREFORMED SHEATH

[75] Inventors: Peter Lawes, Maidenhead; Jacques Vanderlinden, London, both of England

[73] Assignee: Howmedica International, Inc., Shannon, Ireland

[21] Appl. No.: 701,556

[22] Filed: May 16, 1991

[30] Foreign Application Priority Data

May 17, 1990 [GB] United Kingdom ............... 9011132

[51] Int. Cl.⁵ .............................................. A61F 2/36
[52] U.S. Cl. ....................................... 623/23; 623/16; 623/18
[58] Field of Search ................. 623/16, 16 A, 18, 23, 623/22

[56] References Cited

U.S. PATENT DOCUMENTS

| | | | |
|---|---|---|---|
| 4,064,567 | 12/1977 | Burnstein et al. | 623/23 X |
| 4,619,659 | 10/1986 | Witzel | 623/23 |
| 4,670,015 | 6/1987 | Freeman | 623/23 |
| 4,728,335 | 3/1988 | Jurgutis | 623/23 |
| 4,735,625 | 4/1988 | Davidson | 623/23 X |
| 4,753,657 | 6/1988 | Lee et al. | 623/16 |
| 4,888,023 | 12/1989 | Averill et al. | 623/22 |
| 4,919,665 | 4/1990 | Homsy | 623/23 X |
| 5,080,680 | 1/1992 | Mikhail et al. | 623/23 |

FOREIGN PATENT DOCUMENTS

| | | | |
|---|---|---|---|
| 0179626 | 4/1986 | European Pat. Off. | 623/23 |
| 0187903 | 7/1986 | European Pat. Off. | 623/23 |
| 0278807 | 8/1988 | European Pat. Off. | 623/19 |
| 2808740 | 9/1979 | Fed. Rep. of Germany | 623/23 |
| 3802214 | 7/1989 | Fed. Rep. of Germany | 623/23 |
| 9015067 | 1/1991 | Fed. Rep. of Germany | . |
| 8100670 | 3/1981 | PCT Int'l Appl. | . |
| 1409053 | 10/1975 | United Kingdom | 623/22 |
| 1443470 | 7/1976 | United Kingdom | 623/16 A |
| 2052267 | 1/1981 | United Kingdom | . |
| 2104391 | 3/1983 | United Kingdom | 623/16 |
| 2162753 | 2/1986 | United Kingdom | 623/18 |

OTHER PUBLICATIONS

"The Effects of the Collar on Total Hip Femoral Component Subsidence", by Leo A. Whiteside et al, in Clinical Orthopaedics and Related Research, pp. 120–126, Jun. 1988, No. 231.
Brochure from Dow Corning Wright, "Whiteside Total Hip System", 1985.
Brochure from Howmedica, "Exeter Universal Hip System".

Primary Examiner—Ronald Frinks
Attorney, Agent, or Firm—Peter C. Richardson; Lawrence C. Akers; Raymond W. Augustin

[57] ABSTRACT

A prosthetic intramedullary femoral prosthesis provided with a separate preformed sheath made from an acrylic material which is dimensioned to enclose the prosthesis stem from the distal tip to a location on the stem which will be adjacent the proximal cut end of the femur with which it will be used.

11 Claims, 1 Drawing Sheet

PROSTHETIC INTRAMEDULLARY FEMORAL PROSTHESIS WITH PREFORMED SHEATH

BACKGROUND OF THE INVENTION

This invention relates to a prosthetic intramedullary femoral prosthesis provided with a separate preformed sheath and to a preformed sheath for use with such a prosthesis.

Many kinds of prosthetic intramedullary femoral prostheses are held in position in the medullary canal of the femur, in which the prosthesis is implanted by bone cement. In the type of prosthesis in which there is no neck collar, the prosthesis stem can sink further into the cement after fitting and this can cause difficulties in reengagement of the tapering stem. There have been cases where the cement has been squeezed away totally during operative implantation such that there is direct contact between the metal stem and the bone, forming a window in the cement mantle. Such a window is highly undesirable, it can be the source of cracks progressing through the cement mantle and it can be a route by which debris of polyethylene, metal or bone cement can travel down the interface between the stem and the cement and out through the window, where it lodges in the bone and can be a source of bonelysis (bone death or loss of substance).

Various patents have addressed axial movement of the stem after implantation. For example, U.S. Pat. No. 4,888,023 relates to a stem having a distal tip for use in a non-cemented application with a polished outer surface. The tip is intended to be fixed to the distal part of the stem and allow for centralization and the axial sliding between the polished outer surface of the tip and the interior of the intramedullary canal.

U.S. Pat. No. 4,619,659 discloses a femoral component surrounded by a resin sheath. The entire sheath outside surface is solidly cemented into the femur along the full length thereof. The design allows sliding motion between the distal surface portions of the stem and the sheath. U.S. Pat. No. 4,670,015 relates to a hip implant having a distal tip fixedly engaging the distal portion of the stem as can be best seen in FIG. 6 thereof. European Patent Application Publication No. 0187903 A1 relates to a femoral component having a distal sleeve threaded into the medullary canal, which sleeve has a threaded outer surface with an inner polyethylene sleeve to allow sliding engagement between the distal stem portion and the sheath.

U.S. Pat. No. 4,753,657 relates to a hip prosthesis having a distal sleeve fixedly attached to the distal stem. The sleeve has an outer surface which allows the subsidence of the stem within the medullary canal. U.K. Patent 1 409 053 relates to a femoral component having a distal centralizer fixedly attached to the distal stem of the prosthesis. The centralizer allows axial movement within the canal.

An article entitled "The Effects of the Collar on Total Hip Femoral Component Subsidence" by Leo A. Whiteside, David Amador and Kenneth Russell analyzes the effects of avoiding, in a non-cemented application, distal axial loading, i.e. allowing some axial motion, in a collarless prosthesis while having a tight enough fit to prevent the distal end of the prosthesis from moving in a plane perpendicular to the longitudinal axis of the femur.

An advertisement of Dow Corning Wright entitled "Whiteside Total Hip System" relates to an acrylic sleeve which centers a stem in the medullary canal and forms an integral bond to bone cement. Howmedica brochure entitled "Exeter Universal Hip System" relates to a centralizer which fits over the tip of the prosthesis, which centralizer is made from an acrylic material which is dimensioned to enclose the prosthesis stem and allow subsidence of the stem within the acrylic sleeve. A similar sleeve is shown in U.K. Patent GB 2104391.

SUMMARY OF THE INVENTION

The present invention is intended to overcome some of the disadvantages referred to above.

According to the present invention, a prosthetic intramedullary femoral prosthesis is provided with a separate preformed sheath made from an acrylic material which is dimensioned to enclose the prosthesis stem from the distal tip to a location on the stem, which will be adjacent the proximal cut end, i.e. open end, of the femur with which it is used.

By preforming such a sheath, there is reduced adhesion between the cement which holds the stem in place and the polished surface of the stem and thus preferably the sheath is dimensioned and constructed to allow the stem to move further into it under load.

The chances of a window or cracks being formed in the cement mantle is therefore reduced. Preferably, the distal end of the sheath is in the form of a cup, the inner end surface of which is spaced away from the distal end of the prosthesis stem to provide a void when initially located in position to accept subsequent inward movement after fitting. This ensures that the end of the sheath is not pierced by the stem by subsequent movement. The sheath can be made from a material similar to bone cement material, for example, polymethylmethacrylate.

The sheath therefore forms what is, in effect, another layer of cement, but it is not secured to the stem and it does ensure that the stem is completely covered. The thickness of the sheath can be as small as possible, provided it is strong enough not to crack during implantation and, for example, it can be between ½ mm and 5 mm and is preferably about 1 mm for practical use. It will be appreciated that the sheath is molded separately and is shaped to fit a particular size of prosthesis stem.

In a preferred embodiment the sheath is provided with means for centralizing the prosthesis stem in the intramedullary canal and such centralizing means may include outwardly projecting resiliently deformable abutments.

These abutments can be in the form of resilient wings, fins or arms which can deform inwardly and may be arranged to deform substantially radially inwardly or, deform circumferentially inwardly in the manner shown in the co-pending U.S. patent application No. 601,554, filed Oct. 23, 1990, now U.S. Pat. No. 5,092,892.

The invention also includes a preformed sheath for use with an intramedullary femoral prosthesis as set forth above.

BRIEF DESCRIPTION OF THE DRAWINGS

In the drawings wherein similar reference characters denote similar elements throughout the several views.

DETAILED DESCRIPTION OF THE INVENTION

Figure 1:
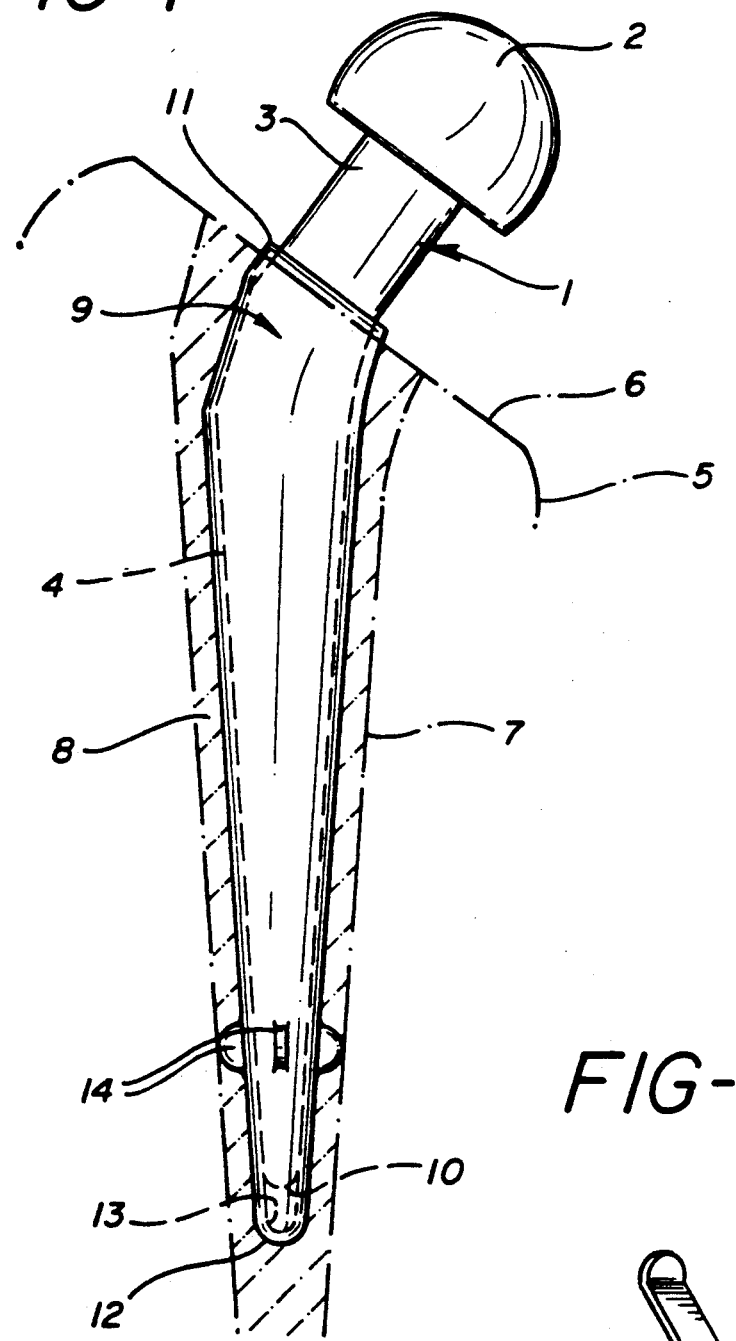
FIG. 1 is a side elevation of an intramedullary femoral prosthesis provided with a sheath according to the invention.

As shown in FIG. 1, an intramedullary femoral prosthesis 1 has a head 2 of known type which is connected through a neck 3 to an intramedullary stem 4. The prosthesis is shown in position in a femur indicated by broken lines 5, the proximal cut end of which is indicated by reference numeral 6. In FIG. 1 the prosthesis 1 is shown in position in the intramedullary canal 7 and is held by bone cement 8.

The stem 4 is enclosed in a sheath 9 which covers the stem from its distal tip 10 to a location adjacent the proximal cut end 6 of the femur 5. In the arrangement shown, this end 11 of the sheath is shown slightly protruding from the cement mantle 8.

The sheath is made from a material similar to bone cement material, for example, polymethylmethacrylate, with a filler to make it more flexible, and its distal end 2 is somewhat longer than the end of the stem 10 to create a void 13.

The thickness of the sheath is about 1 mm and can be made as a separate molding.

Molded into the sheath are four thin outwardly projecting abutments 14 in the form of four equally spaced tangentially projecting wings or arms. These abutments act as a centralizer and to hold the stem 4 away from the wall of the medullary canal during implantation.

The projections can resiliently deform circumferentially inwardly as the stem, together with the sheath, is pushed into place in the canal 7.

With the sheath in position, the centralizer provided by the abutments becomes well integrated with the cement, as does the remains of the sheath, thus avoiding any weakening or hole creation.

If there is now a tendency for the stem to move further into the cement mantle, this is accommodated by movement within the sheath which, it will be appreciated, has become integral with the cement mantle itself, but because it is not connected to the stem, adhesion between the cement and the stem is reduced and therefore the frictional resistance to the subsiding action or reengagement of the stem is reduced.

Figure 2:
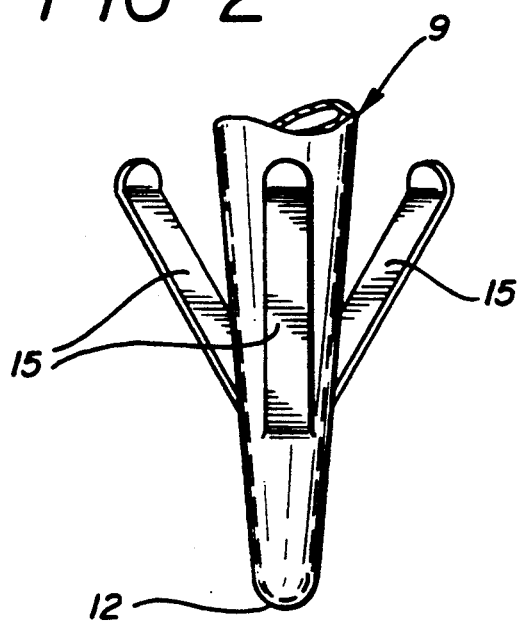
FIG. 2 shows the distal end of a sheath according to a different embodiment.

An alternative construction of the sheath is shown in FIG. 2 and in which similar reference numerals are used to indicate similar parts.

With this arrangement the void 13 is again created when the sheath 9 is placed on the stem 4 (not shown in FIG. 2). In this construction, however, the abutments 14 are provided by three radially and upwardly extending arms 15 spaced around the sheath and which again act to centralize the stem in the medullary canal.

When the prosthesis is to be implanted, the surgeon fits the appropriate size of preformed sheath to the stem of the prosthesis, the sheath including the integrally formed centralizer with a void creator on the distal tip. The assembled stem and sheath are then inserted into the bone cavity which has already been filled with normal bone cement in the normal way. The preformed cement sheath bonds directly with the bone cement inserted by the surgeon. The material of the sheath and the cement are identical or compatible so that they are bonded together.

It is important that the preformed sheath is separate from the stem, it cannot be provided merely by a coating applied to the stem, as this will not give the same low friction characteristics at the surface of the stem which are required.

It is possible to provide a lubricant between the preformed sheath and the stem in order to reduce friction still further, a suitable sterile lubricant being used, for example, sterile liquid paraffin.

The invention is intended to provide an optimization of the interface conditions between the cement in an intramedullary canal and the surface of the stem. The avoidance of windows in the cement and direct contact between metal and bone is also an advantage.

We claim:

1. A prosthetic intramedullary femoral prosthesis comprising a stem and a separate preformed sheath made from an acrylic material which is dimensioned to enclose the prosthesis stem from the distal tip to a location on the stem which will be adjacent the proximal cut end of the femur with which it will be used, said preformed sheath having a shape substantially the same as the stem but extending further in the distal direction to produce a void between the distal tip thereof and the distal tip of the stem, said preformed sheath slidably receiving said stem to allow axial movement therebetween over the length of said stem after implantation, said sheath having a thickness of between 0.5 mm and 2 mm.

2. The prosthetic intramedullary femoral prosthesis as claimed in claim 1 in which the sheath is dimensioned and constructed to allow the stem to move further into it under load.

3. The prosthetic intramedullary femoral prosthesis as claimed in claim 1 in which the distal tip of the sheath is in the form of a cup, the inner end surface of which is spaced away from the distal tip of the prosthesis stem to provide a void when initially located in position, to accept subsequent inward movement after fitting.

4. The prosthetic intramedullary femoral prosthesis as claimed in claim 1 in which the sheath is made from a material similar to bone cement, i.e., polymethylmethacrylate.

5. The prosthetic intramedullary femoral prosthesis as claimed in claim 1 in which the sheath has a thickness of substantially 1 mm.

6. The prosthetic intramedullary femoral prosthesis as claimed in claim 1 in which said sheath is provided with means for centralizing the prosthesis stem in the intramedullary canal of the femur with which it is to be used.

7. The prosthetic intramedullary femoral prosthesis as in claim 6 in which the centralizing means include outwardly projecting resiliently deformable abutments.

8. The prosthetic intramedullary femoral prosthesis as claimed in claim 7 in which the resilient abutments are in the form of resilient wings, fins or arms which can deform inwardly.

9. The prosthetic intramedullary femoral prosthesis as claimed in claim 8 in which the abutments can deform substantially radially inwardly.

10. The prosthetic intramedullary femoral prosthesis as claimed in claim 8 in which the abutments can deform circumferentially inwardly.

11. A prosthetic intramedullary femoral prosthesis comprising a stem and a separate preformed sheath made from an acrylic material which is dimensioned to enclose the prosthesis stem from the distal tip to a location on the stem which will be adjacent the proximal cut end of the femur with which it will be used, said sheath being provided with means for centralizing the prosthesis stem in the intramedullary canal of the femur with which it is to be used, said centralizing means including outwardly projecting resiliently deformable abutments which resilient abutments are in the form of resilient wings, fins or arms which can deform circumferentially inwardly.

* * * * *